United States Patent
Wong

(10) Patent No.: US 8,545,501 B2
(45) Date of Patent: Oct. 1, 2013

(54) INSTRUMENTS FOR PREPARING BONE IMPLANTS

(75) Inventor: Kian-Ming (Kevin) Wong, Cordova, TN (US)

(73) Assignee: Wright Medical Technology, Inc., Arlington, TN (US)

( * ) Notice: Subject to any disclaimer, the term of this patent is extended or adjusted under 35 U.S.C. 154(b) by 1085 days.

(21) Appl. No.: 12/255,855

(22) Filed: Oct. 22, 2008

(65) Prior Publication Data

US 2010/0100097 A1 Apr. 22, 2010

(51) Int. Cl.
*A61B 17/00* (2006.01)
*A61F 5/00* (2006.01)
*A61F 2/46* (2006.01)

(52) U.S. Cl.
USPC ............... 606/79; 606/84; 606/86 R; 606/87

(58) Field of Classification Search
USPC ............... 606/53, 61, 79, 80, 82, 84, 86 R, 606/87, 88, 99, 167, 170, 172, 184, 60, 67, 606/68, 103, 104; 76/28; 142/35
See application file for complete search history.

(56) References Cited

U.S. PATENT DOCUMENTS

| | | | | |
|---|---|---|---|---|
| 5,257,996 A | * | 11/1993 | McGuire | 606/104 |
| 5,380,332 A | * | 1/1995 | Ferrante | 606/79 |
| 5,616,146 A | * | 4/1997 | Murray | 606/80 |
| 5,885,298 A | * | 3/1999 | Herrington et al. | 606/88 |
| 6,174,311 B1 | * | 1/2001 | Branch et al. | 606/86 A |
| 2001/0001121 A1 | * | 5/2001 | Lombardo et al. | 606/89 |
| 2006/0241626 A1 | * | 10/2006 | McGahan et al. | 606/79 |

* cited by examiner

*Primary Examiner* — David Isabella
*Assistant Examiner* — Yashita Sharma
(74) *Attorney, Agent, or Firm* — Duane Morris LLP

(57) ABSTRACT

A system for preparing a bone implant includes a chisel and a cutting guide. The chisel includes a handle includes an elongate body having a distal end and a proximal end. A chisel head is connected to the distal end of the handle. The chisel head includes a stop and a blade distally extending from the stop. The stop defines a notch. A mushroom head radially extends from the proximal end of the handle. The cutting guide has a body defining a cavity and a plurality of slots. The cavity is sized and configured to receive a bone implant. The plurality of slots are each sized and configured to receive the blade of the chisel.

10 Claims, 13 Drawing Sheets

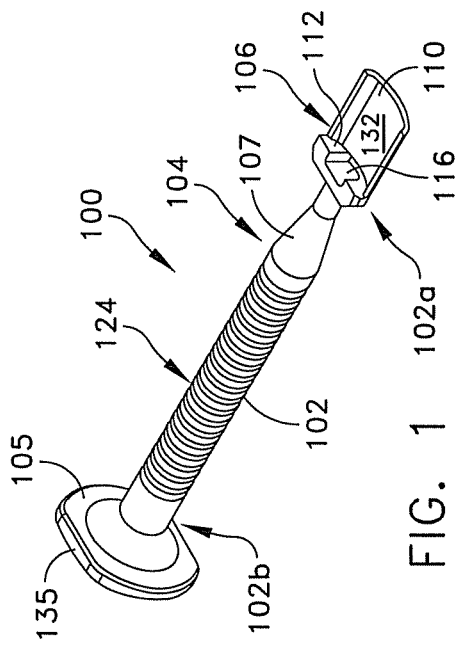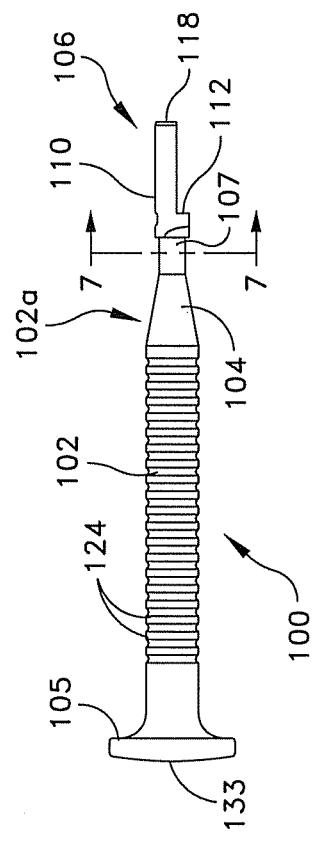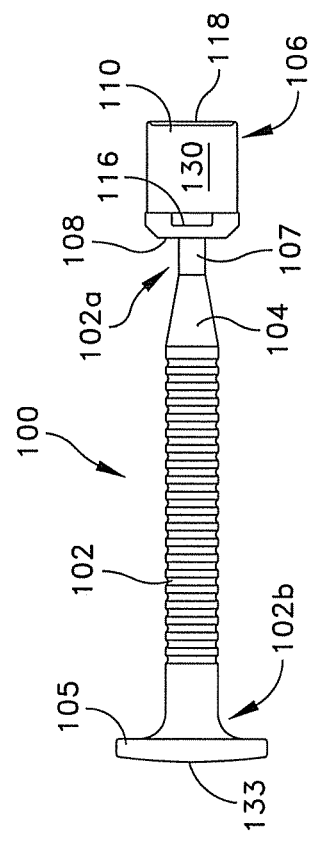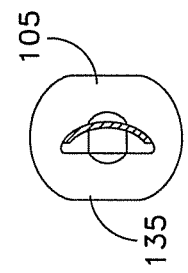

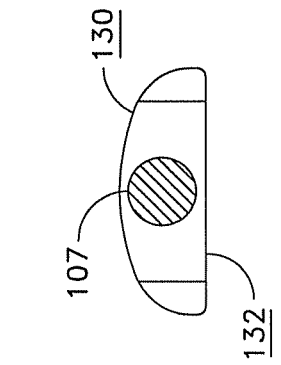
FIG. 5
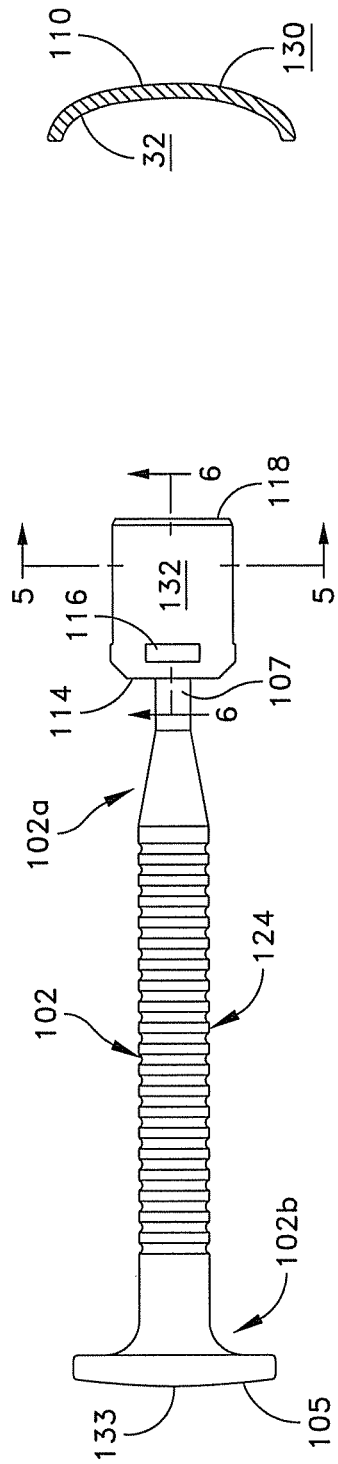
FIG. 3
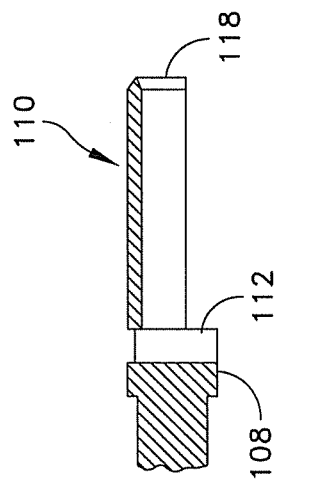
FIG. 7
FIG. 6

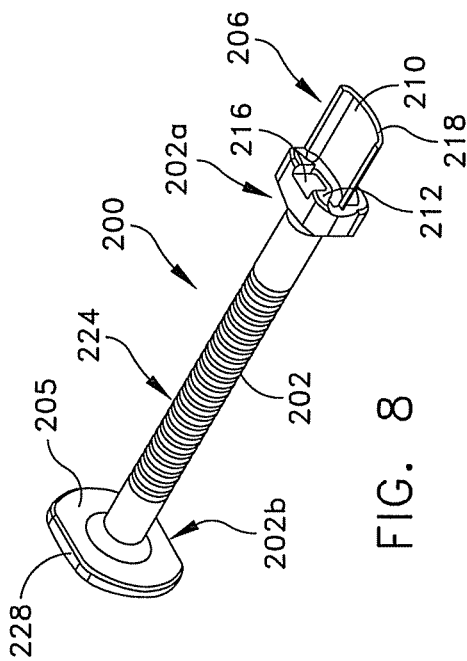
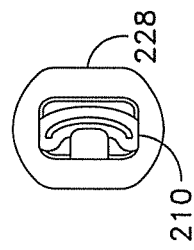
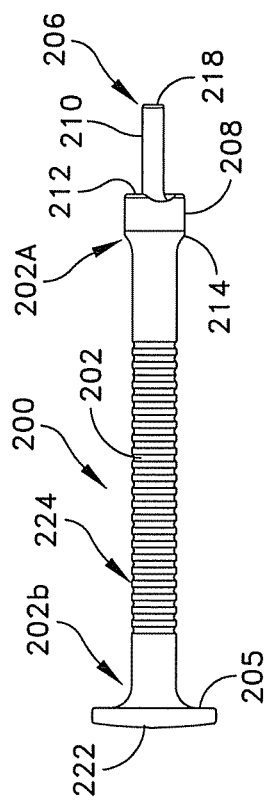
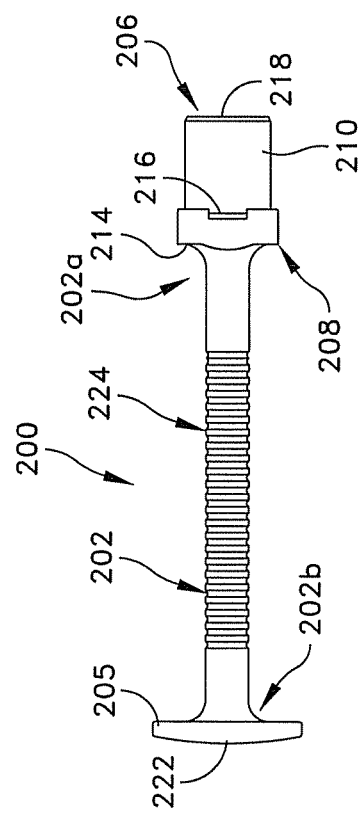

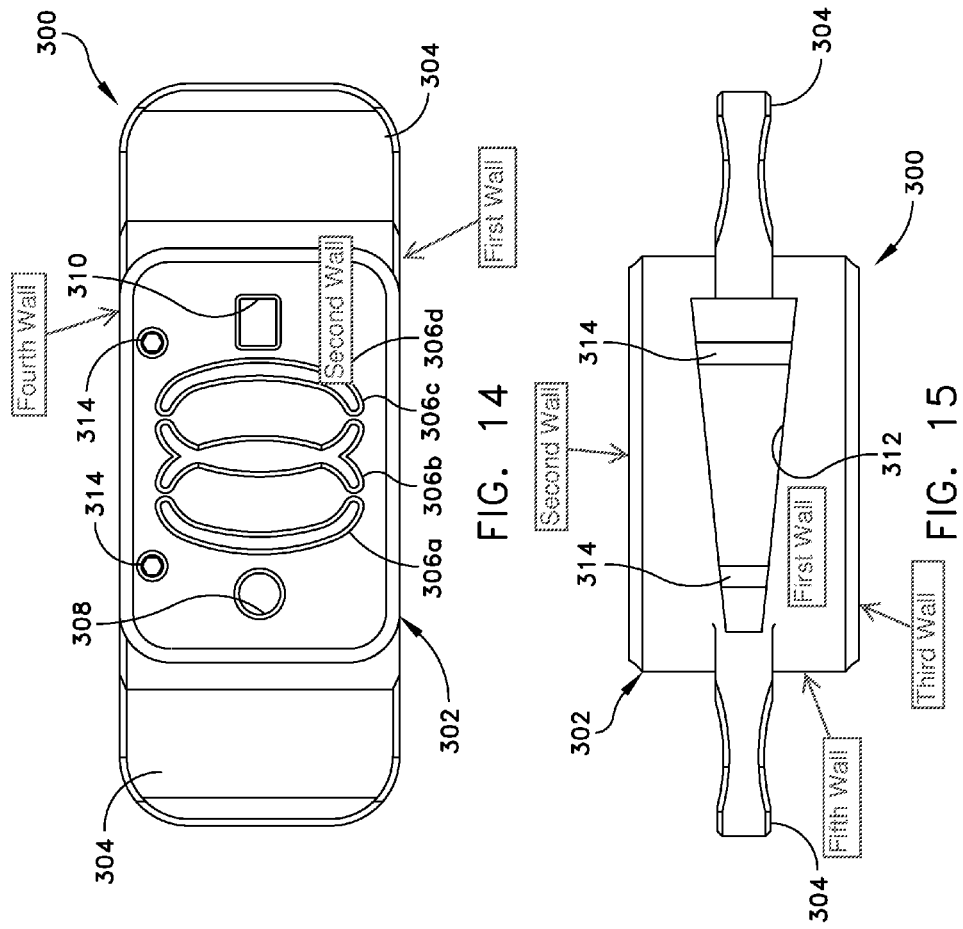

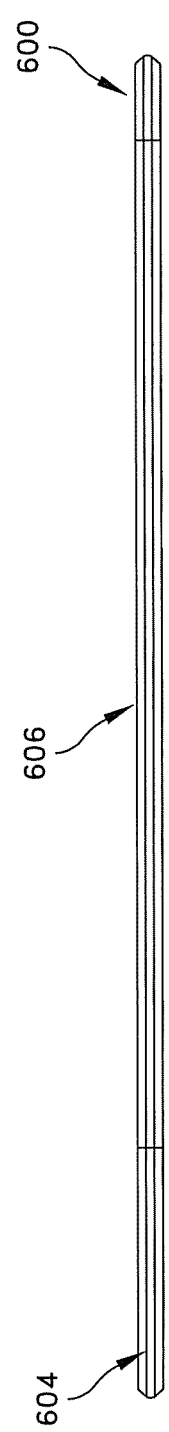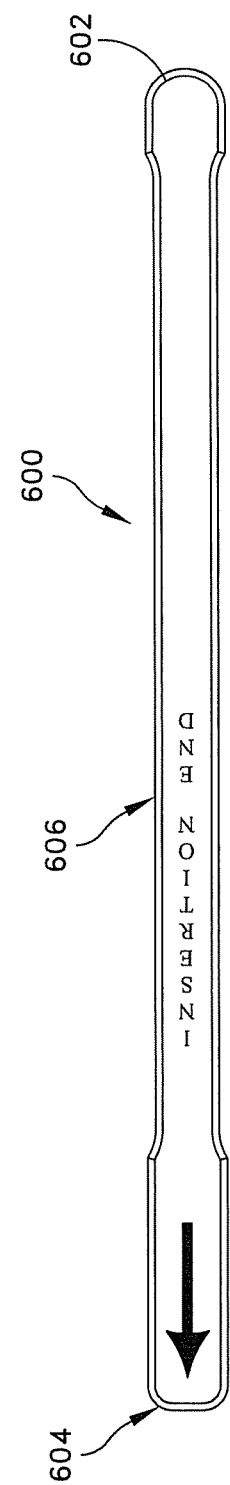

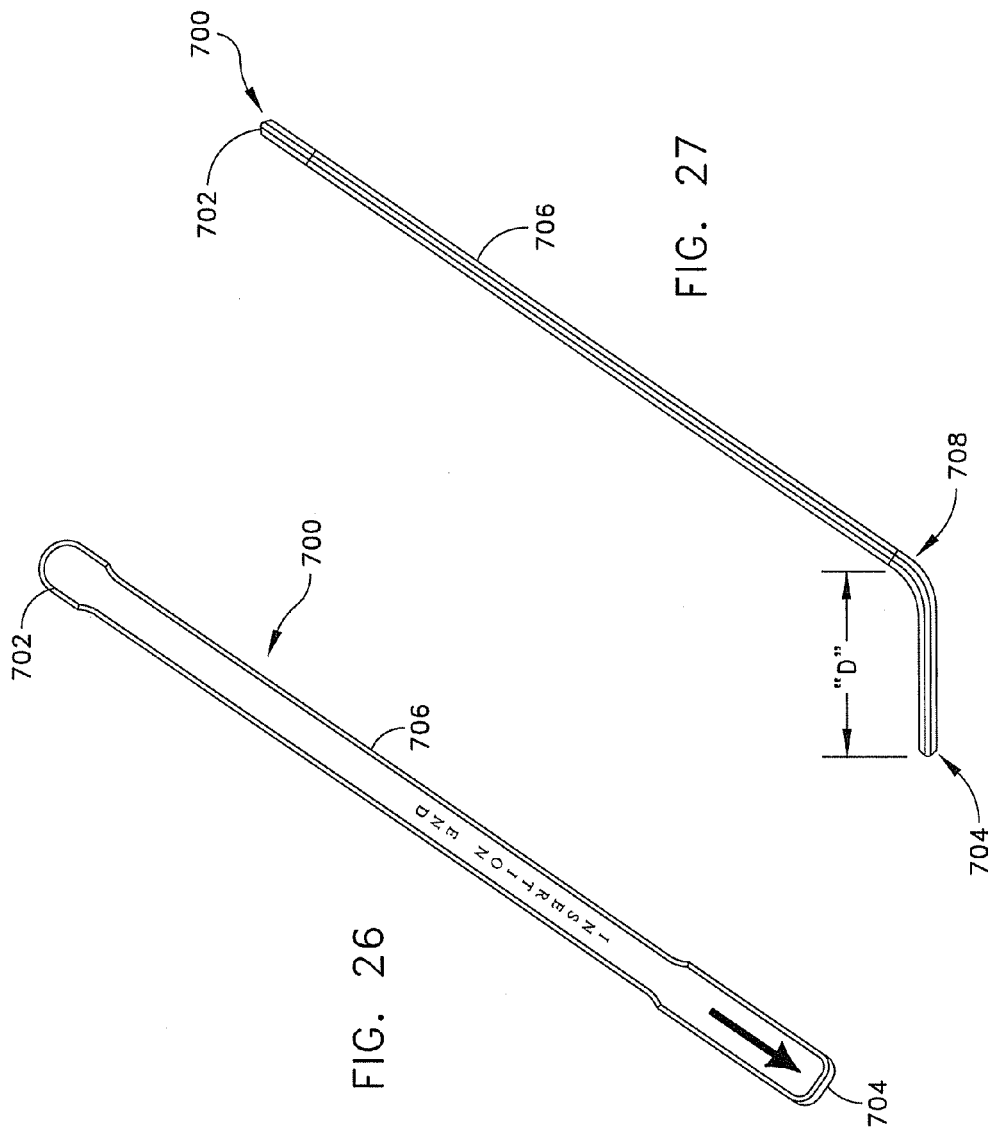

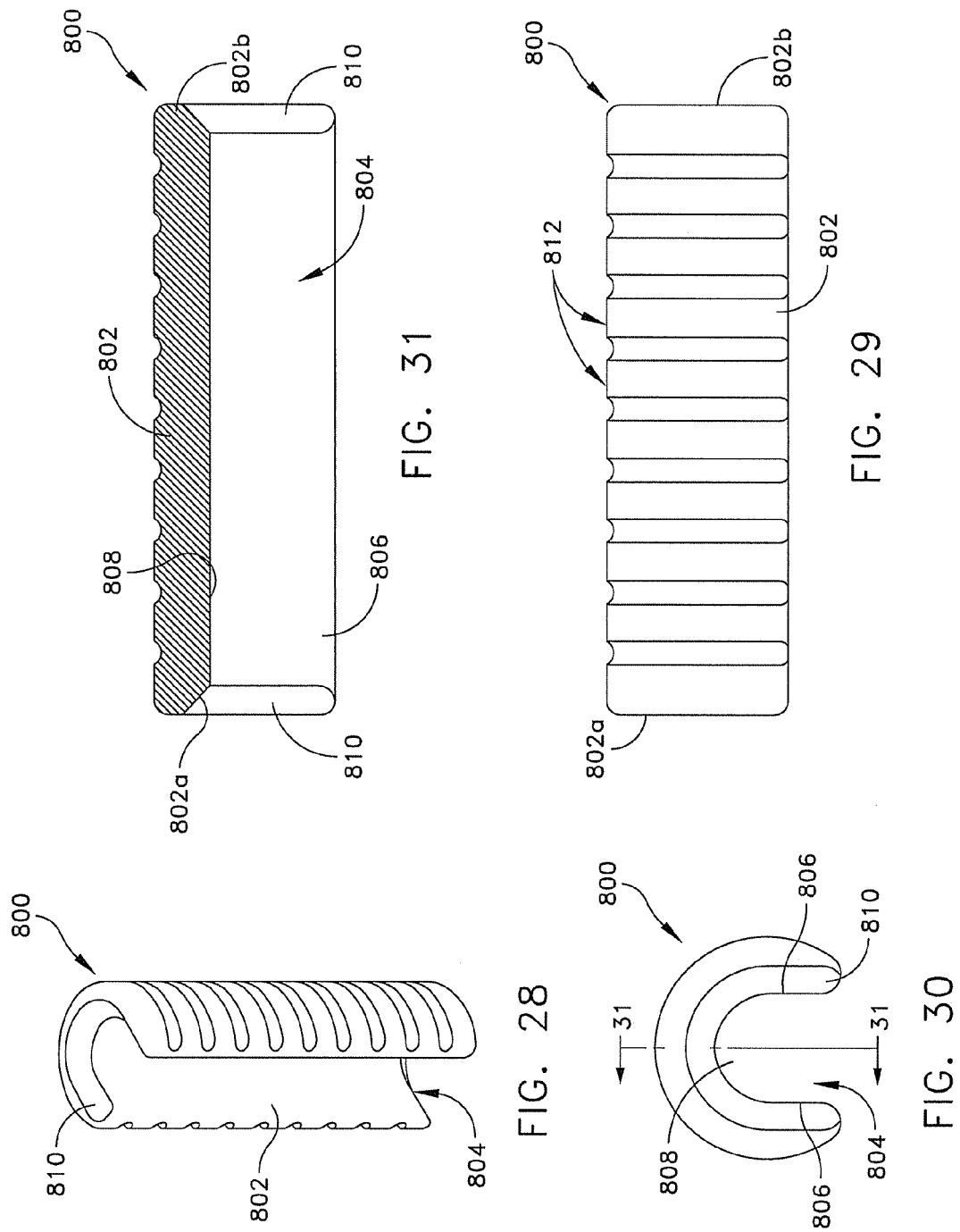

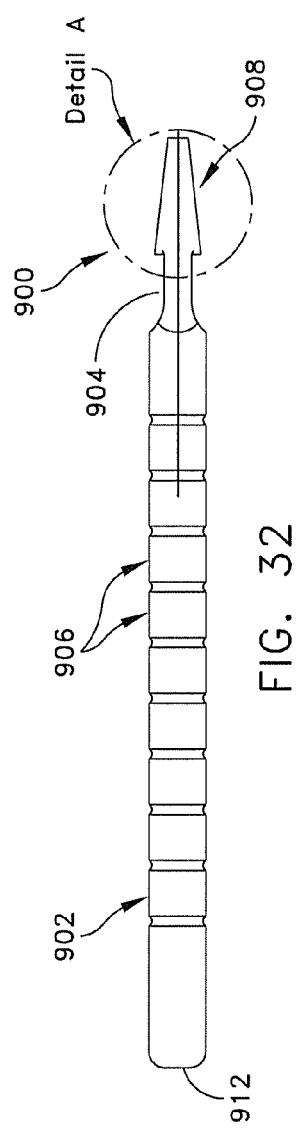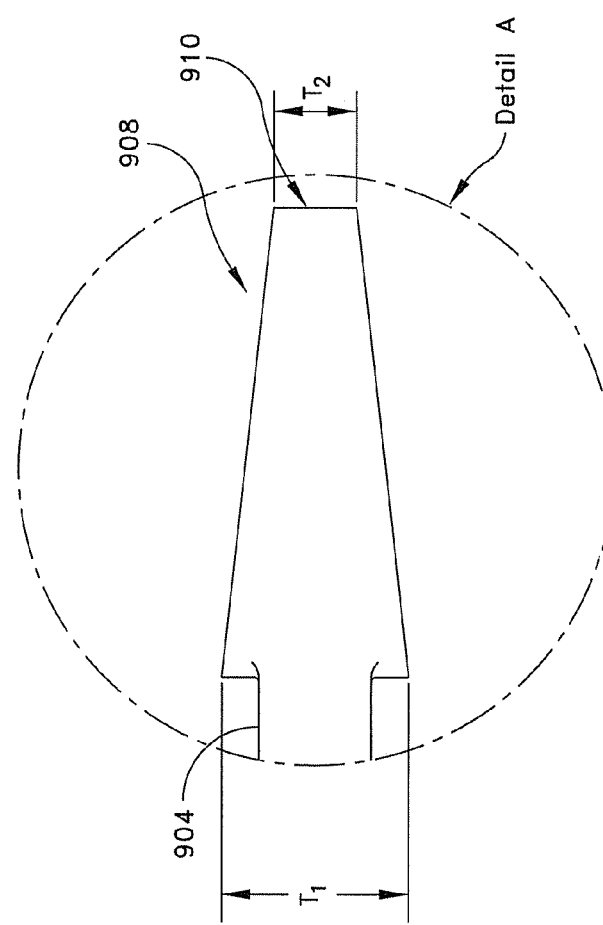

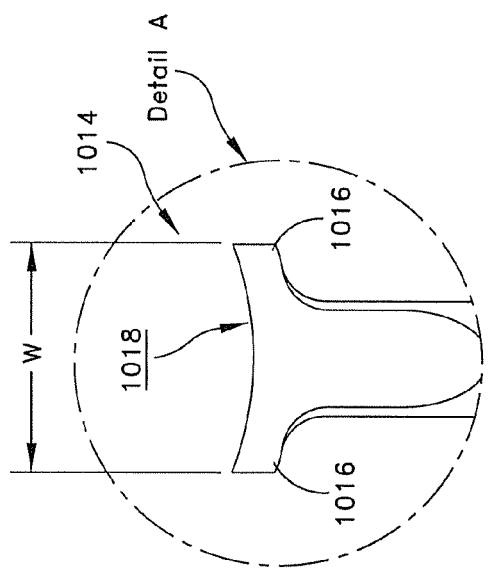
FIG. 37
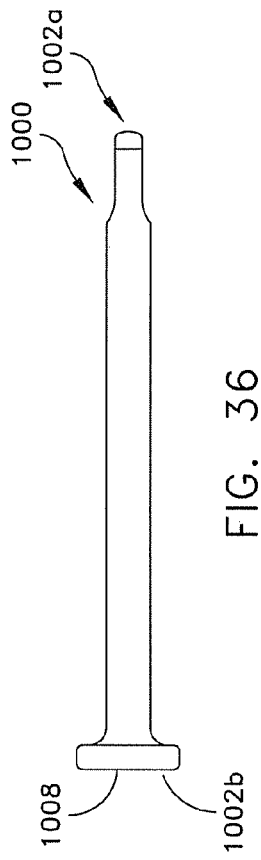
FIG. 36
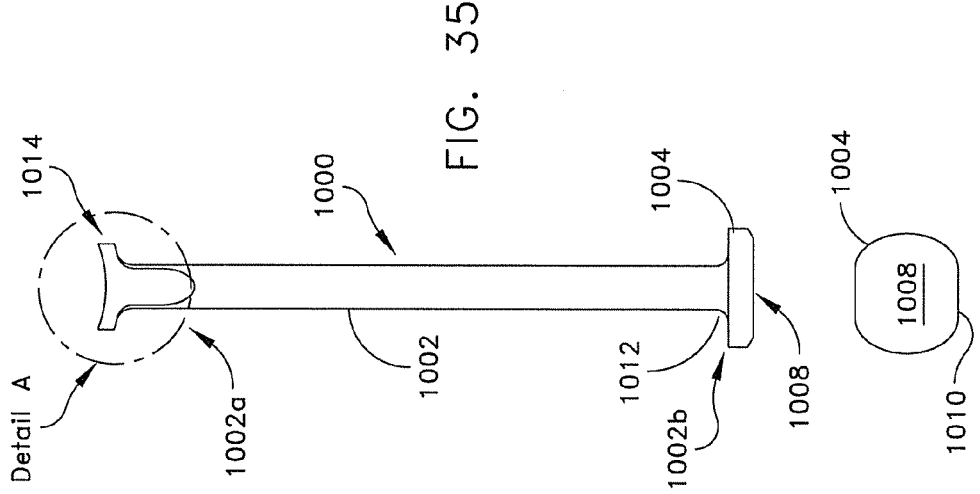
FIG. 35
FIG. 38

INSTRUMENTS FOR PREPARING BONE IMPLANTS

FIELD OF DISCLOSURE

The present invention relates to a system, kit, and method associated with surgical instruments, and more particularly to a system, kit, and method related to surgical instruments for preparing bone implants.

BACKGROUND OF THE INVENTION

Adult acquired flatfoot deformity or posterior tibial tendon dysfunction is a gradual but progressive loss of a person's arch. The posterior tibial muscle is a deep muscle in the back of the calf that has a long tendon that extends from above the ankle and attaches into several sites around the arch of the foot. This muscle acts like a stirrup on the inside of the foot to help support and stabilize the arch and to create a rigid platform for walking and running. If the posterior tibial tendon becomes damaged or tears, then the arch loses its stability and collapses causing a flatfoot. There are various stages of the adult flatfoot deformity. At stage two, deformities usually require a surgical bone procedure to recreate the arch and stabilize the foot. These procedures include isolated fusion procedures, bone grafts, and/or the repositioning of bones through bony cuts called osteotomies.

Various osteotomies for correction of the adult flatfoot have been developed and practiced. One such osteotomy, the Evans procedure, is a calcaneal osteotomy that lengthens the lateral column and realigns the midtarsal joint by reducing forefoot abduction. The Evans procedure also plantarflexes the first metatarsal and reduces talocalcaneal subluxation. Another osteotomy, the Cotton procedure, corrects the flatfoot deformity through a structural graft placed in the medial cuneiform. In both the Evans and Cotton procedures, a bone graft or implant is placed in an osteotomy created in the foot of a patient. Bone implants, such as the CANCELLO-PURE™ Evans and Cotton bone wedges available from Wright Medical Technology, Inc., in Arlington, Tenn., have been created for use in both types of osteotomies. As the size and shape of the foot varies from person to person, it is sometimes necessary for a bone implant to be customized in the operating room (OR) so that the implant appropriately corrects the deformity. However, customizing a bone implant, during a surgical procedure is not easily accomplished as the bone implants are often formed from sterilized animal bone or allograft making them difficult to shape tableside.

SUMMARY OF THE INVENTION

In one embodiment of the present invention, a system for preparing a bone implant comprises a chisel and a cutting guide. The chisel includes a handle having an elongate body including a distal end and a proximal end. A chisel head is connected to the distal end of the handle. The chisel head forms a stop and a blade. The blade extends distally from the stop. The stop is formed by a notch defined in the chisel head. An expanded or "mushroom" head extends radially from the proximal end of the handle. The cutting guide has a body defining a cavity and a plurality of slots. The cavity is sized and configured to receive a bone implant. The plurality of slots are each sized and configured to receive the blade of the chisel.

In another embodiment of the invention, a kit for preparing a bone implant comprises a chisel, a cutting guide, a first cutting template, and a chisel removal tool. The chisel includes a handle comprising an elongate body having a distal end and a proximal end. A chisel head includes a blade connected to the distal end of the handle. An expanded or "mushroom" head extends radially from the proximal end of the handle. The cutting guide has a body defining a cavity and a plurality of slots. The cavity is sized and configured to receive a bone implant. The plurality of slots are each sized and configured to receive the blade of the chisel. The first cutting template has a body defining a slot and is configured for engagement with the cutting guide such that the slot of the first cutting template aligns with one of the plurality of slots of the cutting guide. The chisel removal tool is sized and configured to engage the chisel.

BRIEF DESCRIPTION OF THE DRAWINGS

These and other features and advantages of the present invention will be more fully disclosed in, or rendered obvious by, the following detailed description of the preferred embodiments of the invention, which are to be considered together with the accompanying drawings wherein:

FIG. 1 is a perspective view of a chisel for preparing a bone implant formed in accordance with present invention;

FIG. 2 is a side elevational view of the chisel for preparing a bone implant shown in FIG. 1;

FIG. 2a is a bottom elevational view of the chisel shown in FIGS. 1 and 2;

FIG. 3 is a top plan view of the chisel for preparing a bone implant shown in FIG. 1;

FIG. 4 is a distal-end-on view of the chisel for preparing a bone implant shown in FIG. 1;

FIG. 5 is a cross-sectional view of the chisel for preparing a bone implant as taken along line 5-5 in FIG. 3;

FIG. 6 is a cross-sectional view of the chisel for preparing a bone implant as taken along line 6-6 in FIG. 3;

FIG. 7 is a cross-sectional view of the chisel for preparing a bone implant as taken along line 7-7 in FIG. 2;

FIG. 8 is a perspective view of another chisel for preparing a bone implant in accordance with the present invention;

FIG. 8a is a bottom elevational view of the chisel shown in FIGS. 8 and 9;

FIG. 9 is a side view of the chisel for preparing a bone implant shown in FIG. 8;

FIG. 11 is a distal-end-on view of the chisel for preparing a bone implant shown in FIG. 8;

FIG. 14 is a top side elevational view of a cutting guide in accordance with the present invention;

FIG. 15 is a side view of the cutting guide shown in FIG. 14;

FIG. 24 is a top plan view of a chisel removal tool in accordance with the present invention;

FIG. 25 is a side view of the chisel removal tool shown in FIG. 24;

FIG. 26 is a top plan view of another chisel removal tool in accordance with the present invention.

FIG. 27 is a side view of a chisel removal tool shown in FIG. 26;

FIG. 28 is a perspective view of a slap-hammer chisel remover in accordance with the present invention;

FIG. 29 is a side view of the slap-hammer chisel remover as shown in FIG. 28;

FIG. 30 is an end-on view of the slap-hammer chisel remover shown in FIG. 28;

FIG. 31 is a cross-sectional view of the slap-hammer chisel remover as taken along line 31-31 in FIG. 30;

FIG. 32 is a side view of a trial tool in accordance with the present invention;

FIG. 34 is a detail view of detail A shown in FIG. 32;

FIG. 35 is a top plan view of an impactor in accordance with the present invention;

FIG. 36 is a side view of the impactor shown in FIG. 35;

FIG. 37 is a detail view of the detail A in FIG. 35; and

FIG. 38 is a proximal end view of the impactor shown in FIG. 36.

DETAILED DESCRIPTION OF PREFERRED EMBODIMENTS

Figure 12:
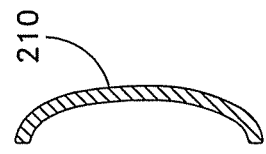
FIG. 12 is a cross-sectional view of the chisel for preparing a bone implant as taken along line 12-12 in FIG. 10.
Figure 10:
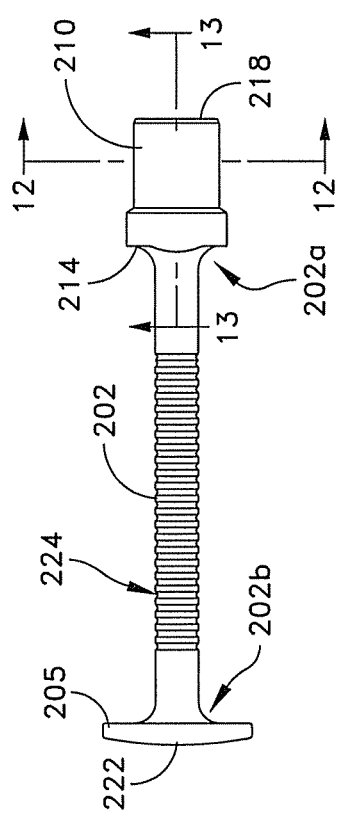
FIG. 10 is a top plan view of the chisel for preparing a bone implant shown in FIG. 8.
Figure 13:
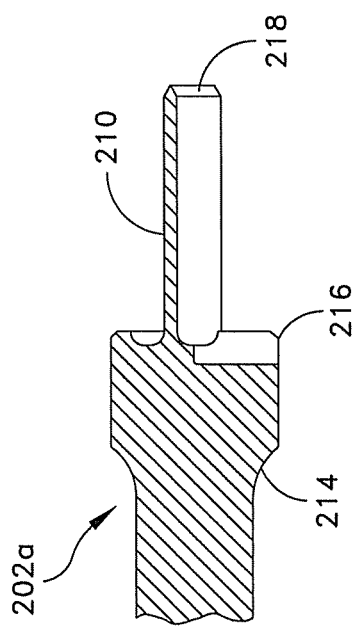
FIG. 13 is a cross-sectional view of the chisel for preparing a bone implant as taken along line 13-13 in FIG. 10.
Figure 16:
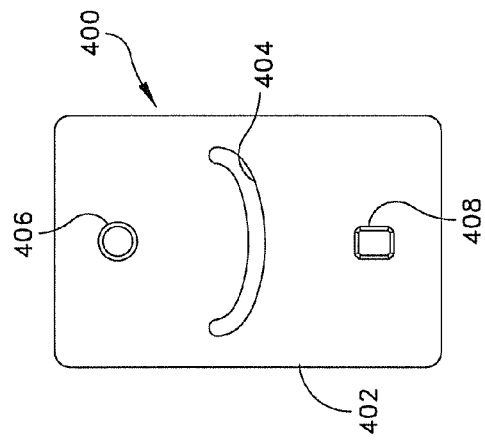
FIG. 16 is a bottom side elevational view of a cutting template in accordance with the present invention.
Figure 17:
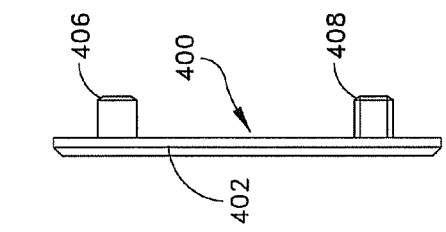
FIG. 17 is a side view of the cutting template shown in FIG. 16.
Figure 18:
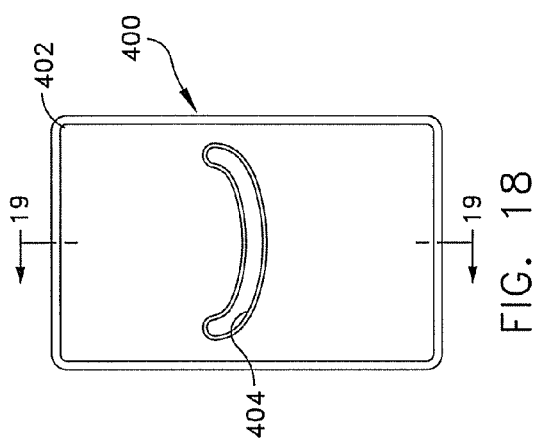
FIG. 18 is a top side elevational view of the cutting template shown in FIG. 16.
Figure 19:
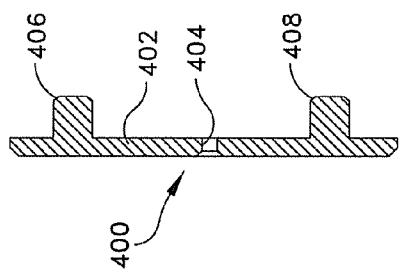
FIG. 19 is a cross-sectional view of the cutting template as taken along line 19-19 in FIG. 18.
Figure 20:
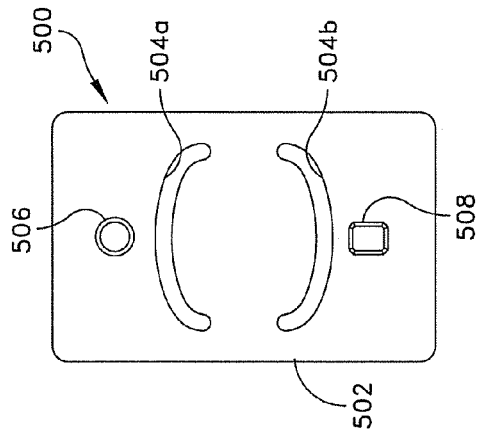
FIG. 20 is a bottom side elevational view of another cutting template in accordance with the present invention.
Figure 21:
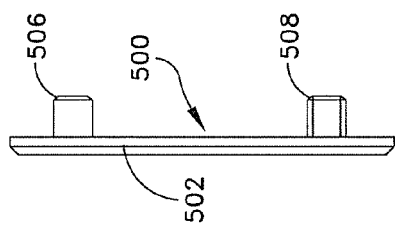
FIG. 21 is a side view of the cutting template shown in FIG. 20.
Figure 22:
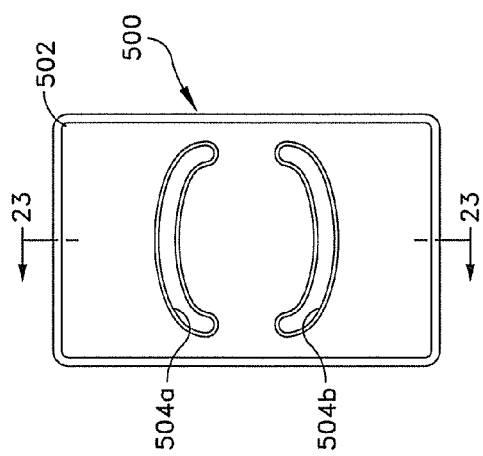
FIG. 22 is a top side elevational view of the cutting template shown in FIG. 20.
Figure 23:
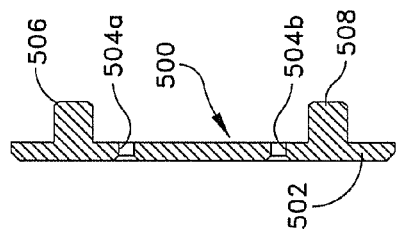
FIG. 23 is a cross-sectional view of the cutting template as taken along line 23-23 in FIG. 20.

This description of the preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In the description, relative terms such as "horizontal", "vertical", "up", "down", "top", and "bottom" as well as derivatives thereof (e.g., "horizontally", "downwardly", "upwardly", etc.) should be construed to refer to the orientation as then described or as shown in the drawing figure under discussion. These relative terms are for convenience of description and normally are not intended to require a particular orientation. Terms including "inwardly" versus "outwardly", "longitudinal" versus "lateral" and the like are to be interpreted relative to one another or relative to an axis of elongation, or an axis or center of rotation, as appropriate. Terms concerning attachments, coupling and the like, such as "connected" and "interconnected", refer to a relationship wherein structures are secured or attached to one another either directly or indirectly through intervening structures, as well as both movable or rigid attachments or relationships, unless expressly described otherwise. The instruments and methods are described by way of example as being used to shape and customize a bone implant that is to be inserted into an osteotomy formed in the foot of a patient. However, this description is for exemplary purposes and should not be construed to limit the scope of use of the disclosed instruments and methods.

Referring to FIGS. 1-7, a chisel 100 for preparing a bone implant formed in accordance with the present invention is often formed from any biocompatible, engineering material that is suitably rigid and hard so as to be capable of shaping a bone implant without bending, breaking, or chipping, e.g., stainless or high carbon steel. Chisel 100 includes a handle 102 having a distal end 102a and a proximal end 102b (FIG. 1). A chisel head 106 is located at distal end 102a, and a transversely expanded or "mushroom" head 105 located at a proximal end 102b. Handle 102 may have a circular or polygonal cross-sectional shape often with a width dimension that provides sufficient structural integrity to prevent unwanted bending or breaking while fitting comfortably in the hand of a surgeon. Referring to FIG. 2, handle 102 includes a frustoconical neck 104 at distal end 102a which has a substantially cylindrical portion 107 that projects outwardly from its distal end so as to connect to or engage with a rear portion of chisel head 106. Although shown as having a tapering cross-sectional shape, in some embodiments, neck portion 104 may have a constant cross-sectional shape that is larger or smaller than the cross-sectional shape of handle 102. Handle 102 may include knurling or circumferentially arranged ribs 124 disposed along a substantial portion of its length to increase the ability of a surgeon to hold and manipulate chisel 100 without it slipping. Knurling or circumferentially arranged ribs 124 may take the form of a plurality of concentric notches formed along the length of handle 102, or may be replaced altogether or partially by a roughened surface.

Chisel head 106 includes a stop 108 and a blade 110 (FIG. 2a). The cross-sectional shape of blade 110 includes a convexly curved top surface 130 and a substantially planar bottom surface 132 (FIGS. 2a and 7). Stop 108 extends radially from cylindrical portion 107, and includes a face 112 and a contact surface 114. Face 112 of stop 108 defines a rectangular notch 116 having a width and length that together enable another tool to engage chisel head 106, as will hereinafter be disclosed in further detail. Notch 116 often has a rectangular shape, one skilled in the art will appreciate that notch 116 may have any geometry that facilitates engagement with another tool. In some embodiments, notch 116 extends transversely relative to the longitudinal axis of handle 102, and often communicates with bottom surface 132, although in some embodiments notch 116 may not communicate with bottom surface 132. Blade 110 extends distally from face 112 of stop 108, and has a curved cross-sectional geometry (FIG. 5). In some embodiments, the blade has a curved cross-sectional geometry that emulates the curvature of the lateral side of a calcaneus. The distal tip of blade 110 is swaged so as to taper to a cutting edge 118 that is suitable for cutting or shaping a bone implant (FIG. 6). Referring to FIGS. 2, 2a, and 3, mushroom head 105 includes a proximal face 133 that may be used as a force bearing surface if additional force is needed to shape a portion of the bone implant. Mushroom head 105 may have any geometry including, but not limited to, circular, oval, hexagonal, or rectangular. Mushroom head 105 may include one or more flats 135 to prevent chisel 100 from rolling when placed on its side (FIG. 1).

Referring to FIGS. 8-13, a chisel 200 formed in accordance with the present invention includes a handle 202 having a distal end 202a and a proximal end 202b. A chisel head 206 is located at distal end 202a, and a transversely expanded or "mushroom" head 205 located at a proximal end 202b. Chisel handle 202 may have a circular or polygonal cross-sectional shape often with a width dimension that provides sufficient structural integrity to prevent unwanted bending or breaking while fitting comfortably in the hand of a surgeon. Chisel handle 202 may include knurling or circumferentially arranged ribs 224 disposed along a substantial portion of its length to increase the ability of a surgeon to hold and manipulate chisel 200 without slippage.

Referring to FIG. 9, chisel head 206 includes a stop 208 having a rectangular cross-sectional shape that is greater than the cross-sectional shape of handle 202. A rectangular notch 216 is formed in a distal face 212 of stop 208 (FIG. 8). One skilled in the art will appreciate that notch 216 may have other geometries in addition to a rectangular geometry. Chisel head 206 includes a blade 210 that extends distally from a central portion of stop 208. Referring to FIGS. 11 and 12, blade 210 may have a curved cross-section. In some embodiments, the curved cross-section of blade 210 complements the curvature of the lateral side of a calcaneus. The distal end of blade 210 is swaged so as to taper to a cutting edge 218 that is suitable for cutting or shaping a bone implant. The proximal side of stop 208 defines a contact surface 214. Proximal end 202b of handle 202 is connected to mushroom head 205, and includes a proximal face 222, and one or more flats 228 to prevent chisel 200 from rolling when placed on a surface (FIGS. 8 and 11).

Referring to FIGS. 14 and 15, a cutting guide 300 formed in accordance with the present invention includes a body 302 including first, second, third, and fourth walls and having a pair of tabs 304 extending from a fifth wall that is disposed perpendicular to the first, second, third and fourth walls. Each of tabs 304 extend outwardly from a side of body 302 in longitudinally aligned, spaced relation to one another. Cutting guide 300 is often formed any biocompatible, engineering material that is suitably rigid and hard so as to be capable of withstanding compressive loads. Examples of such materials include, but are not limited to stainless steel and carbon steel. As shown in FIG. 15, tabs 304 may have a thickness that is less than the thickness of the body 302. One skilled in the art will appreciate that the thickness of tabs 304 may be varied to enable a person to hold and easily manipulate cutting guide 300.

An implant cavity 312 is defined by the first, second, third, fourth and fifth walls and by a trapezoidal recess formed within body 302 of cutting guide 300 (FIG. 15). Implant cavity 312 is often sized and configured to accept a wedge-shaped bone implant 10 such as, for example, a CANCELLO-PURE™ Evans Bone Wedge available from Wright Medical Technology, Inc., of Arlington, Tenn. In some embodiments, implant cavity 312 has a height, length, and depth that is suitable for receiving such a wedge-shaped bone implant having a height of approximately 12 mm, a length of approximately 28 mm, and a width of approximately 22 mm. One skilled in the art will appreciate that the geometry and dimensions of implant cavity 312 may be adjusted to be larger or smaller to accommodate bone implants of various shapes and sizes. One or more alignment guides 314 extend across implant cavity 312. In one embodiment, alignment guides 314 may comprise a pair of pins that are press fit into holes defined by body 302 of cutting guide 300. In other embodiments, alignment guides 314 may comprise fewer or more pins or be formed as one or more prongs or projections that serve to properly align a bone implant within implant cavity 312.

As shown in FIG. 14, a top surface of cutting guide 300 also defines a plurality of curved openings that communicate with inwardly extending passageways that each create a curved slot 306a, 306b, 306c, and 306d. The curvature of slots 306a, 306b, 306c, and 306d is selected so as to be complementary to the curvature of either blade 110 or blade 210. Curved slots 306a, 306b, 306c, and 306d are spaced apart from one another, and are often arranged in body 302 at graduated locations. In some embodiments, curved slots 306a, 306b, 306c, and 306d extend through body 302 of cutting guide 300 so as to allow communication between a top surface and a bottom surface of body 302. Internal openings in the walls of body 302, that define implant cavity 312, communicate with corresponding portions of curved slots 306a, 306b, 306c, and 306d so as to be positioned longitudinally along implant cavity 312, and graduated with respect to one another. In this way, a bone implant that has been positioned within implant cavity 312 may be cut to one of several predetermined sizes by insertion of one of chisel 100 or chisel 200 into successive ones of curved slots 306a, 306b, 306c, and 306d. For example, a bone implant may be cut using slots 306a and 306d to create a bone implant having a thickness of 10 mm, slot 306b to create a bone implant having a thickness of 8 mm, and slot 306c to create a bone implant having a thickness of 12 mm. One skilled in the art will appreciate that slots 306 may be provided in different locations of the body 302 to yield bone implants with a variety of dimensions as necessary or desirable for a particular procedure or patient. Cutting guide 300 also defines a round mounting hole 308 and a rectangular or square mounting hole 310 that are each formed in the body 302. In one embodiment, mounting holes 308 and 310 extend through the entire body 302 of cutting guide 300, and have different cross-sectional geometries. One skilled in the art will understand that cutting guide 302 may have fewer or more mounting holes.

Referring to FIGS. 16-19, when a surgeon wishes to pre-select a particular implant length to be shaped with the present invention, a cutting template 400 may be placed over the top surface of cutting guide 300 so as to block all but one or two of curved slots 306a, 306b, 306c, and 306d. More particularly, a cutting template 400 often has a rectangular body 402 including substantially flat top and bottom surfaces. A pair of spaced-apart studs 406, 408 project outwardly in substantially perpendicular relation from the bottom surface of body 402. One skilled in the art will understand that the number of studs may be varied depending on the number of mounting holes are provided in cutting guide 300. The top surface of cutting template 400 also defines a curved opening that communicates with an inwardly extending passageway and another correspondingly located opening in the bottom surface of cutting template 400. In this way, a curved slot 404 is formed that extends through body 402. Curved slot 404 has a shape that corresponds to any one of curved slots 306a, 306b, 306c, and 306d. Studs 406, 408 project outwardly from the bottom surface of cutting template 400. In the embodiment illustrated in FIGS. 16-17, stud 406 has a substantially circular cross-sectional shape corresponding to the cross-sectional shape of round mounting hole 308, while stud 408 has rectangular or square cross-sectional shape that corresponds to the cross-sectional shape of rectangular or square mounting hole 310 such that the cutting template 400 is keyed to the cutting guide 300 regardless of the side to which the cutting template 400 is installed. One skilled in the art will appreciate that other geometries and sizes of studs 406 and 408 may be provided with adequate effect. When cutting template 400 mounted to cutting guide 300, such that stud 406 is received within round mounting hole 308 and stud 408 is received within rectangular or square mounting hole 310, curved slot 404 may be quickly identified by a surgeon or other user as the remaining slots on cutting guide 300 will be covered by body 402 of cutting template 400. Additionally, cutting template 400 may be numbered to identify the size of bone implant to be formed by its use. For example, a cutting template 400 may be labeled "10" (not shown) if a bone implant with a thickness of 10 mm is formed by its use.

Referring to FIGS. 20-23, another cutting template 500 includes a body 502, one or more studs 506, 508, and two curved slots 504a, 504b that are formed in substantially similar fashion to cutting template 400. Slots 504a, 504b are provided at locations on body 502 of cutting template 500 that will align with slots 306a and 306d of cutting guide 300 when cutting template 500 is installed on cutting guide 300 in a manner substantially similar to that of cutting template 400. One skilled in the art will appreciate that the location of slots 504a, 504b may be varied so that the bone implant is cut to the desired dimensions.

Referring to FIGS. 24 and 25, a chisel remover 600 includes a proximal end 602, a distal or insertion end 604, and a handle portion 606. Proximal end 602 and insertion end 604 may have a width that is the smaller than, greater than, or equal to a width of the handle portion 606. In one embodiment, chisel remover 600 may have a substantially constant thickness with upper and lower surfaces being substantially straight. The insertion end 604 is sized such that it may be received within notch 116, 216 of chisel 100, 200. Chisel remover 600 may be formed from any suitable a biocompatible engineering material that has sufficient strength to be used to pry chisel 100, 200 from cutting guide 300. Examples of such materials include, but are not limited to titanium, carbon steel, and stainless steel.

Referring to FIGS. 26 and 27, another embodiment of chisel remover 700. As shown in FIG. 27, chisel remover 700 may have a curved cross-sectional profile 708 at or near a distal end 704 to enhance leverage. In one embodiment, the curve or bend 708 is located at a distance "D" from distal end 704 so that the curve 708 pivots on a top surface of the cutting template 400, 500 or cutting guide 300 when the distal end is inserted into the slot 116, 216 of chisel 100, 200. One skilled in the art will appreciate that the distance D may be varied up to and including half the length of the total length of the chisel remover 700 so as to change the length of the lever arm.

Referring to FIGS. 28-31, a slap-hammer chisel remover 800 has a curved body 802 that defines a channel 804. Channel 804 is defined between two longitudinally extending side walls 806 and a radiused base 808. An edge portion of each of the ends 802a, 802b of body 802 may include a chamfer 810 to facilitate engagement with handle 102, 202 of chisel 100, 200. Frictional elements 812 may be formed on the outer surface of slap-hammer chisel remover 800 to provide a gripping surface for a surgeon. Frictional elements 812 may be formed by a series of notches in the outer surface of body 802 or any roughened or knurled surface that provides enhanced friction to facilitate gripping by a surgeon or other user. Slap-hammer chisel 800 may be formed from any material that has sufficient structural integrity to resist bending, breaking, or chipping when used. Examples of materials include, but are not limited to, titanium, carbon steel, and stainless steel.

Figure 33:
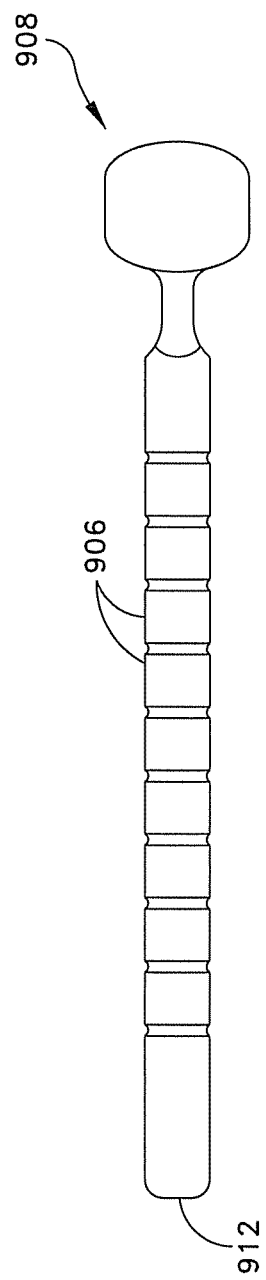
FIG. 33 is a top plan view of the trial tool shown in FIG. 32.

Referring to FIGS. 32-34 a trial 900 may be formed from any material that has sufficient durability to be placed into and be removed from an osteotomy formed in a patient's foot. In some embodiments, trials 900 are formed from a metallic material to provide contrast during a fluoroscopic imaging procedure. Examples of such metallic materials include, but are not limited to, aluminum, stainless steel, high-carbon steel, and titanium. Trial 900 includes an elongate handle 902 and a trial head 908. Elongate handle 902 may include a neck portion 904 that connects to trial head 908. Neck portion 904 may have a reduced cross-sectional area relative to the cross-sectional area of elongate handle 902 to provide clearance when inserting and removing trial 900 from an osteotomy. Elongate handle 902 may also include frictional elements 906 disposed along the length of handle 902. In one embodiment, frictional elements 906 may take the form of a plurality of concentric notches formed in the outer surface of handle 902. In other embodiments, frictional elements 906 may be a roughened or knurled surface of the handle 902. In one embodiment, a proximal end 912 of handle 902 may be substantially flat to provide a striking surface for a hammer or other concussive instrument to facilitate insertion of trial head 908 into an osteotomy. In other embodiments, trial 900 may include a mushroomed or broadened head or other feature that facilitates insertion into and/or removal of trial head 908 from an osteotomy.

Trial head 908 has a trapezoidal cross-sectional profile that tapers from a thickness, $T_1$, adjacent neck portion 904 of handle 902 to a distal end 910 having a thickness $T_2$ (FIG. 34). Examples of the thickness $T_1$ of trial head 908 include, but are not limited to 8 mm, 10 mm, and 12 mm. In one embodiment, thickness $T_2$ of distal end 910 of trial head 908 may vary depending upon the thickness $T_1$ as the bone wedge implants are preformed and distal end 910 is formed to replicate the distal end of a bone implant. The corners of trial head 908 may be rounded to facilitate insertion and removal of trial head 908 into and out of an osteotomy without catching on or tearing skin, ligament, or other soft tissue. As shown in FIG. 33, trial head 908 has a substantially rectangular cross-section, often with rounded corners. In one embodiment, the length of trial head 908 is substantially equal to the length of the bone implant that will be placed within an osteotomy in, e.g., a patient's foot.

Referring to FIGS. 35-38, an impactor 1000 includes a handle 1002, a mushroomed or broadened head 1004, and an impacting end 1014. Handle 1002 has a proximal end 1002b and a distal end 1002a. Mushroom head 1004 radially extends from the proximal end 1002b of handle 1002. Mushroom head 1004 includes a proximal face 1008 that may be used as a force bearing surface if additional force is needed to drive the bone implant into an osteotomy. Mushroom head 1004 may have any geometry including, but not limited to, hexagonal, circular, oval, or rectangular. As shown in FIG. 38, mushroom head 1004 may include one or more flats 1010 to prevent impactor 1000 from rolling when placed on a surface. A radius or chamfer 1012 may be formed between mushroom head 1004 and handle 1002 to provide an ergonomic fit with the hand of a surgeon or user.

Impacting end 1014 is disposed at proximal end 1002b of handle 1002. In one embodiment and as shown in FIG. 36, impacting end 1014 has a smaller thickness than the thickness of handle 1002. In some embodiments, the thickness of impacting end 1014 is greater than or equal to the smallest thickness of the wider end of a prepared bone implant to enable impactor 1000 to impact a bone implant such that the entire bone implant fits within the osteotomy. For example, if a bone implant has a wide end of 8 mm, then the thickness the impacting end 1014 is equal to or less than 8 mm.

Referring now to FIG. 37, impacting end 1014 may include extensions 1016 that extend outwardly from handle 1002. However, in some embodiments, impactor 1000 does not include extensions 1016. Impacting end 1014 may define a concave surface 1018 between the extensions 1016. The curvature of the concave surface is complementary with the curvature of the blade 110, 210 of chisel 100, 200. In some embodiments, the width W of impacting end 1014 is less than or equal to the width of a bone implant. However, one skilled in the art will appreciate that the width W of the impactor 1000 may be varied.

The instruments for preparing bone implants may be included in a kit. The kit may include one or more trials 900 that may be used by a surgeon or other operating room personnel to determine the size of a bone implant that will be inserted into an osteotomy created in a foot of a patient. For example, the kit may include a trial 900 for an implant having a thickness of 8 mm, 10 mm, and 12 mm. The kit may also include a chisel 100, 200 for cutting and shaping a bone implant. A cutting guide 300 for facilitating the cutting of the bone implant with chisel 100, 200 along with one or more cutting templates 400, 500 may also be included in the kit. A chisel remover 600, 700, 800 may also be included in the kit to aid in the removal of the chisel 100, 200 from the cutting guide 300 after a bone implant has been shaped. Additionally, an impactor 1000 may be included to assist in the insertion of the sized bone implant into the osteotomy located in the patient's foot.

Referring to FIGS. 1-38, a method for preparing a bone implant is now described. A surgeon performing an Evans procedure may make an oblique incision centered over the distal lateral calcaneus while avoiding the intermediate dorsal cutaneous nerve superiorly and the sural nerve inferiorly. The depth of the incision may be increased through the superficial fascia to expose the lateral surface of the calcaneus. A cut may be made through the calcaneus using a sagittal saw approximately one to one and a half centimeters proximal to the calcaneocuboid joint.

A spreader may then be used to open the osteotomy and lengthen the lateral column. Once the lateral column is lengthened, a trial 900 may be inserted into the osteotomy. With the trial located in the osteotomy, the distractor may be loosened. In some instances, the trial 900 with the smallest thickness, e.g., a thickness of 8 mm, may be inserted into the osteotomy. Forefoot correction and talonavicular coverage may be determined fluoroscopically with the trial 900 still located within the osteotomy. If additional correction or coverage is needed, the trial 900 is removed and a trial having a larger thickness, e.g., 10 mm or 12 mm, is inserted. With a trial 900 having a larger thickness located within the osteotomy, the forefoot correction and talonavicular coverage may again be fluoroscopically checked.

Once the sizing of the implant is determined, the cutting template 400, 500 corresponding to the size of the trial 900 that is determined to provide the desired correction and coverage is installed to the cutting guide 300. For example, if it is determined that the 10 mm trial 900 provides the desired amount of forefoot correction and talonavicular coverage, then the 10 mm cutting template 500 is selected and the round protrusion 506 and square protrusion 508 of cutting template 500 are placed into the corresponding round and square mounting holes 308, 310 of cutting guide 300. A wedge-shaped bone implant may be placed within the implant cavity 312 of cutting guide 300 either before or after the cutting template 400, 500 is installed to the cutting guide 300.

With the bone implant located within the implant cavity 312, a chisel 100, 200 may be used to cut the bone implant to the desired size. For example, the blade 210 of chisel 200 may be first placed into slot 504a of the cutting template 500 that aligns with slot 306a of the cutting guide 300. The blade 210 is slid into the slots 504a and 306a so that the cutting surface 218 of the chisel 200 makes contact with the wedge-shaped bone implant. A force is applied along the axis of the chisel 200 so that the blade 210 extends through and severs the bone implant.

A mallet, hammer, or other tool may be used to strike the proximal face 222 of the mushroom head 205 of chisel 200 until the distal face 212 of stop 208 makes contact with the cutting template 500. Alternatively, the slap-hammer chisel remover 800 may be used to apply an impact force along the axis of the chisel 200. To use the slap hammer 800, the channel 804 of the slap-hammer 800 is placed around the handle 202 of the chisel 200. Note that the channel 804 is sized to receive the handle 202 of chisel 200 slidably therein.

Once the handle 202 of the chisel 200 is disposed in the channel 804 of the slap-hammer 800, the surgeon may slide the slap-hammer 800 from an initial position located near the mushroom head 205 towards the chisel head 206 so that an end 802a, 802b of slap-hammer 800 contacts the contact surface 214 of the stop 208. If required, the slap-hammer 800 may be repeatedly slid along the handle 202 of the chisel 200 to make contact with the proximal face 214 of stop 208 until the blade 210 of chisel 200 severs the bone implant. The blade 210 of chisel 200 is sized to ensure that it will fully cut through the wedge-shaped bone implant, but will not protrude through the opposite side of cutting guide 300.

Once the chisel 200 severs the bone implant, the blade 210 is withdrawn from slots 306a and 504a of the cutting guide 300 and cutting template 500, respectively. In some instances it may be difficult to remove the blade 212 of the chisel 200 from the slots of the cutting guide 300 and cutting template 500. In these instances, a chisel remover 600, 700 may used to remove the chisel 200 from the cutting guide 300. To remove chisel 200 from cutting guide 300 using chisel remover 700, the distal end 704 of chisel remover 700 is inserted into the notch 216 located in the stop 208 of the chisel 200. The distal end 704 of chisel remover 700 is inserted into the notch 216 such that handle portion 706 protrudes from the surface of the body 302 of cutting guide 300 at an angle. A force perpendicular to the top surface of the cutting guide 300 may then be applied to the proximal end 702 of chisel remover 700. One or more of the tabs 304 of the cutting guide 300 may be held to maintain the cutting guide 300 in a fixed position. The application of force to the proximal end 702 of the chisel remover 700 works to pry to chisel 200 from slot 504a of the cutting template 500 and slot 306a of cutting guide 300.

Alternatively, the slap-hammer chisel remover 800 may be used to remove chisel 200 from the slots of the cutting guide 300 and cutting template 500. The channel 804 of slap-hammer 800 is placed around the handle 202 of chisel 200. With the handle 202 of chisel 200 disposed within the channel 804 of slap-hammer 800, the surgeon or user slides the slap-hammer 800 from an initial position located near the stop 208 towards the mushroom head 205 so that an end 802a, 802b of the slap-hammer body 802 contacts the mushroom head 205. If required, the slap-hammer 800 may be repeatedly slid along the handle 202 such that the slap-hammer makes contact with the mushroom head 220 of chisel 200 until the blade 210 of chisel 200 is free from the cutting guide 300 and cutting template 500.

Once the chisel 200 is dislodged from the cutting guide 300 and cutting template 500, the bone implant may be cut a second time using slot 504b of the cutting template 500 and slot 306d of the cutting guide 300 as guides. The process of cutting the bone implant a second time is similar to the process described above with respect the first cut using slots 504a and 306a as guides. Once the bone implant has been shaped, it is removed from the cutting guide 300. If additional shaping of the implant is needed, a bone rongeur, sagittal saw, or the chisel 200 may be used to further shape the implant.

The implant is then inserted into the osteotomy. The impactor 1000 may be used to facilitate the placement of the shaped implant in the osteotomy. For example, the thinner end of the bone implant may be introduced into the osteotomy and then the impactor 1000 may be used to advance the implant into the desired location. To advance and position the implant within the osteotomy, the impacting end 1014 of the impactor 1000 is placed against the exposed surface of the implant. As described above, the concave surface 1018 of the impacting end 1014 has a curvature that is similar to the curvature of the blade 210 of the chisel 200, and thus the cut surface of the bone implant will be engaged by the concave surface 1018 of the impactor 1000. The surgeon or user may then apply a force parallel to the axis of the impactor handle 1002 to advance the implant into the osteotomy. In some instances, a hammer, mallet, or other instrument may be used by the surgeon to strike the proximal face 1008 of the mushroom head 1004 of the impactor 1000 to aid in the advancement of the bone implant into the osteotomy. Desirably, the implant should be located in the osteotomy such that its exterior edge is flush with the host bone.

The impactor 1000 may also be used to adjust the dorsal and plantar position of the bone within the osteotomy. For example, if the wedge is disposed within the osteotomy such that the exterior surface of the implant is flush with the host bone, but the implant is not centered within the bone, then the impactor 1000 may be used to center the implant. The impactor 1000 may be used to center the implant within the osteotomy by applying a force to the impactor 1000 in a similar manner as described above with the exception that the impactor 1000 is not centered on the exterior surface of the implant. The extensions 1016 of the impactor 1000 enable the impactor 1000 to reach a side of the implant while the implant is disposed within the osteotomy. Additionally, since the width of the impacting end 1014 is less than or equal to the thickness of the thickness of the implant, the extensions 1016 are able to be advanced along a side of the implant without contacting bone.

Once the implant is positioned at the desired location within the osteotomy, a plate or other fixation device may be installed across the osteotomy to prevent the implant from backing out of the osteotomy. The incision may then be closed using conventional methods known in the art.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A system for preparing a bone implant, comprising:
   a chisel comprising:
      as handle comprising an elongate body having a distal end and a proximal end;
      a chisel head connected to the distal end of the handle, the chisel head including a stop and a blade, the blade distally extending from the stop, the stop defining a notch; and
      a mushroom head radially extending from the proximal end Of the handle; and
   a cutting guide having a body including first, second, third, and fourth walls that together define a cavity that is accessible via an opening defined by the first wall, a plurality of slots defined by the second wall that is disposed opposite the third wall and adjacent to the first wall, the plurality of slots being in communication with the cavity that is sized and configured to receive a bone implant therein,
   wherein each of the plurality of slots is complementarily sized to and configured to receive the blade of the chisel, and each of the plurality of slots is located at a different location along the second wall to facilitate cutting a bone implant into one of a plurality of sizes, and a cutting template having a body defining a slot, the cutting template configured to be engaged with the cutting guide such that the slot of the cutting template aligns with one of the plurality of slots of the cutting guide and at least one of the plurality of slots defined by the cutting guide is covered by the cutting template.

2. The system of claim 1 further comprising:
   a chisel remover including a body having a distal end and a proximal end, wherein the distal end is sized and arranged to be received within the notch of the chisel.

3. The system of claim 1 further comprising:
   a chisel remover including a body defining a channel, the channel configured to be slidably disposed around the handle of the chisel.

4. The system of claim 1 wherein the blade of the chisel has a curvature configured to emulate the lateral side of a calcaneus.

5. The system of claim 1 wherein the cutting guide includes at least one tab extending from a fifth wall of the body that is disposed perpendicular to the first, second, third, and fourth walls of the body.

6. The system of claim 1 wherein the cutting guide includes at least one alignment guide, the alignment guide configured to locate the bone implant within the cutting guide.

7. The system of claim 1, wherein the cutting template includes at least one stud extending from a bottom surface that is sized and configured to be received within at least one mounting hole defined by the second wall of the body of the cutting guide for mating the cutting template to the cutting guide.

8. The system of claim 1, wherein the cutting template includes a first stud and a second stud, the first stud having a different geometry than the second stud.

9. The system of claim 8, wherein the second wall of the cutting guide defines a first mounting hole having a geometry that is complementary to the first stud of the cutting template and a second mounting hole having a geometry that is complementary to the second stud of the cutting template.

10. The system of claim 6, wherein the at least one alignment guide includes a pin that is disposed within a hole defined by the second wall of the cutting guide body.

* * * * *